(12) United States Patent
Motter et al.

(10) Patent No.: US 6,454,763 B1
(45) Date of Patent: Sep. 24, 2002

(54) LASER SURGICAL HANDPIECE WITH PHOTON TRAP

(75) Inventors: Thomas F. Motter, Sandy; Todd H. Smith, North Salt Lake; Robert M. Millar, Salt Lake City, all of UT (US)

(73) Assignee: Paradigm Medical Industries Inc., Salt Lake City, UT (US)

( * ) Notice: Subject to any disclaimer, the term of this patent is extended or adjusted under 35 U.S.C. 154(b) by 0 days.

(21) Appl. No.: 09/368,737

(22) Filed: Aug. 5, 1999

(51) Int. Cl.7 ................................................ A61B 18/18
(52) U.S. Cl. .............................. 606/16; 606/15; 607/92
(58) Field of Search .............................. 606/4, 5, 6, 16, 606/17–19; 604/240, 275, 35

(56) References Cited

U.S. PATENT DOCUMENTS

| | | | | |
|---|---|---|---|---|
| 3,865,113 A | * | 2/1975 | Sharon et al. ............ | 128/303.1 |
| 4,266,547 A | * | 5/1981 | Komiyya ..................... | 606/15 |
| 4,573,979 A | * | 3/1986 | Blake .......................... | 604/240 |
| 4,685,458 A | * | 8/1987 | Leckrone .................... | 606/15 |
| 4,694,828 A | | 9/1987 | Eichenbaum ............ | 128/303.1 |
| 4,966,596 A | * | 10/1990 | Kuntz et al. .................... | 606/7 |
| 4,985,027 A | * | 1/1991 | Dressel ......................... | 606/15 |
| 4,988,163 A | * | 1/1991 | Cohen et al. ................. | 606/15 |
| 5,026,366 A | * | 6/1991 | Leckrone ....................... | 606/7 |
| 5,112,339 A | * | 5/1992 | Zelman ....................... | 606/107 |
| 5,263,950 A | * | 11/1993 | L'Esperance, Jr. ............. | 606/6 |
| 5,324,282 A | | 6/1994 | Dodick ........................ | 606/15 |
| 5,745,626 A | * | 4/1998 | Duck et al. .................... | 385/96 |
| 5,833,683 A | * | 11/1998 | Fuller et al. .................. | 606/17 |
| 5,906,611 A | | 5/1999 | Dodoick et al. .............. | 606/16 |
| 6,190,381 B1 | * | 2/2001 | Olsen et al. ................... | 606/32 |

OTHER PUBLICATIONS

Ekdahl, "New Laser Phaco," *Eyecare Technology*, pp. 19–21, May/Jun. 1994.

* cited by examiner

Primary Examiner—Michael Peffley
Assistant Examiner—P. J. Vrettakos
(74) Attorney, Agent, or Firm—Madson & Metcalf

(57) ABSTRACT

A laser surgical device for removal of intraocular tissue including a handpiece and a tip. The handpiece has a sleeve that creates a passage way for irrigation fluid. An optic fiber or similar light conveying means is contained within the handpiece. A passageway for aspiration is included in the handpiece and continues into the tip. The tip is configured with a photon trap that captures stray laser light and prevents it from continuing into the eye.

13 Claims, 3 Drawing Sheets

LASER SURGICAL HANDPIECE WITH PHOTON TRAP

1. FIELD OF THE INVENTION

The present invention relates to the field of laser surgical instruments for use in optical surgery. More particularly, the present invention relates to a device that uses laser light to ablate ocular tissue, while at the same time minimizing potential damage to the eye during surgery by providing a structure which is capable of trapping laser light used in the surgical procedure.

2. TECHNICAL BACKGROUND

The eye has an anterior chamber and a posterior chamber which are separated by a normally transparent lens. The lens is a clear tissue located behind the pupil. The lens works with the transparent cornea, which covers the eye's surface, to focus light on the retina at the back of the eye. The lens of the eye is clear at birth, but is one of the first parts of the body to show the effects of aging. If the lens becomes cloudy, light cannot pass to the retina properly and vision is blurred and decreased. This clouding of the lens is known as a cataract.

As the lens becomes increasingly cloudy, light rays are prevented from passing through the lens and focusing on the retina. Early lens changes may not disturb vision. But as the lens continues to change, several specific symptoms may develop including blurred vision, sensitivity to light and glare, increased nearsightedness, or distorted images.

Cataracts are the leading cause of vision loss among adults age 55 and older. The most common cause of cataracts is aging. However, cataracts can affect all ages because they can result from injury, heredity, chronic eye disease, or system-wide diseases such as diabetes.

Sometimes, the cataract stops developing in its early stages, and vision is only slightly decreased. But if it continues to develop, vision is impaired, and treatment is necessary. Surgery to remove the cataract is the only effective treatment.

Cataract surgery has been practiced over a long period of time. In the earliest known technique the cataract was displaced to lie in the vitreous cavity in the back of the eye. Other ancient techniques included breaking up the cataract with a needle to facilitate absorption by the body, and removing the lens from the eye by applying pressure. The displacement or removal of the lens enabled the patient to see better. However, vision was still blurred because the patient lacked a lens to focus light.

In modern cataract surgery the cataract is extracted from the eye. In most cases the lens is replaced with a foldable lens implant inserted into the capsular bag. The lens unfolds within the bag during the surgical procedure in order to replace the natural lens taken out. With the insertion of the replacement lens, the patient is able to focus light as well as benefitting from the removal of the cataract. Thus, vision can be effectively restored to a normal state.

Cataract surgery has become quite common in the United States and other nations. The increasing incidents of cataract surgery has been due in part to the development of improved surgical instruments and techniques. Some of the improved instruments include the operating microscope with coaxial illumination. In addition, surgical instruments have been developed which provide simultaneous irrigation and aspiration for use in closed eye microsurgical systems. It will be appreciated that fluid pressure must be maintained within narrow limits in order to avoid damage to the eye. Therefore, devices which provide both aspiration and irrigation have been an important advance in ocular surgery.

Instrumentation of this type can operate through a small incision in the eye. Typically the incision is approximately 3–4 mm in length. Using this type of instrumentation cataract surgery is performed in which the cortical material of the lens is aspirated. However, the hard nucleus of the lens must be fragmented first and then aspirated.

One device which fragments the cataract is called a phacoemulsifier. This type of device uses an ultrasonically driven vibrating needle as a means of breaking up the cataract. A liquid flows to the surgical site and is aspirated along with the lens fragments. Although phacoemulsification is an improvement over earlier methods because it can be performed through a small incision, the surgical procedure is difficult and requires highly specialized surgical skills. In addition to the need to carefully control fluid flow through the surgical site, the heat and the vibration of the ultrasonic needle can damage adjacent ocular tissue. Clearly heat and vibration must be carefully controlled during the surgery. Thus, this technique has been found to be less than ideal and improvements in technique and equipment have been sought.

With the advent of the surgical laser, lasers have been adapted for use in ocular surgery. It has been found that the use of lasers in cataract surgery has somewhat alleviated the problems of ultrasonic phacoemulsification. With the use of lasers it is possible to construct the hand piece such that it is less bulky and more easily manipulated by a surgeon. This allows more surgeons to gain skill sufficient to manipulate the laser devices. At the same time, the laser does not create sonic vibrations that may cause damage to other tissue so that the risk of damage to the eye is reduced. Finally, there is less heat generated in the eye with the laser devices.

Even though the use of lasers in ocular surgery represents a large advance, there are still problems which arise. While heat and vibration are reduced over that experienced in ultrasonic phacoemulifiers, laser devices have the potential of damaging surrounding tissue through the generation of excess heat or release of deflected light and misdirected high energy laser beams. One problem arises from the fact that as laser light exits an optical fiber, the beam is dispersed. This stray light and other laser light that passes through the target tissue unabsorbed will continue beyond the surgical site. Such light, especially since it is generated by a relatively high powered laser, has the potential of damaging the eye and other tissues if not contained.

Attempts to control stray reflected light and misdirected laser beams have been largely ineffective. Traditionally, the control of misdirected light relies on the skill of the surgeon, not on any specific features designed into the surgical instrument.

In recent years laser surgical devices have been developed which attempt to control the passage of the laser beyond the surgical site. One such device has included a tip which extends distally from the point at which laser light is delivered to the surgical site. The tip extends outwardly and then turns upwardly such that it meets the laser beam exiting the fiber optic. In this manner, the laser beam is deflected such that the full strength of the laser beam does not pass beyond the surgical site. Even in this type of device, however, there is a danger of reflected or disbursed light causing damage, in that the tip of the device simply reflects and disburses the laser beam and provides no means to capture the light. Furthermore, at certain energy levels, the laser light can damage the reflecting tip itself.

Another deficiency of the prior laser devices relates to the configuration and positioning of the irrigation, aspiration, and laser systems. It will be appreciated that it is difficult to simultaneously deliver laser light and fluid to a surgical site, while at the same time providing fluid aspiration from the site. In certain device configurations, these functions can actually oppose one another. In such systems the various functions work against the other requiring more energy to break up the lens. At the same time, difficult design problems are presented in delivering the necessary functions to the surgical site in a manner that is easily controlled and directed by the surgeon. Existing systems are generally less than ideal in that regard.

Accordingly, it would be an advancement in the art to provide a surgical device which began to overcome the problems identified above. In particular, it would be an advancement in the art to provide a laser surgical handpiece which was capable of efficiently delivering laser light, irrigation, and aspiration to the surgical site. It would be a further advancement in the art to provide such a handpiece which included a structure capable of minimizing dispersed laser energy and reflected light beyond the surgical site. It would also be an advancement in the art to provide such a device which would collect stray laser light and remove the energy from the eye, and that would use irrigation and suction to complement the action of the laser. It would be an advancement in the art to provide such a laser surgical device which could be easily manipulated by a surgeon.

Such a device is disclosed and claimed below.

3. BRIEF SUMMARY OF THE INVENTION

The present invention relates to the field of laser surgical instruments for use in optical surgery. More particularly, the present invention relates to a device that uses laser light to ablate ocular tissue, while at the same time minimizing potential damage to the eye during surgery. The present invention provides a laser surgical device for removal of intraocular tissue and specifically the removal of cataract lens tissue.

The device of the present invention includes a handpiece. The handpiece is sized and configured in much the same manner as conventionally accepted laser surgical handpieces. On the proximal end of the handpiece are the necessary connections and ports to run the device. These include a connection for receiving a laser beam generated by an external surgical laser of the type generally used in the field of ocular surgery. The laser connection in turn connects to an optical fiber which is capable of carrying the laser beam distally through the handpiece.

The handpiece also includes irrigation fluid and aspiration connections. Once again, these connections are similar to known devices and use conventional Luer connections. These connections are in turn in fluid communication with an aspiration channel and an irrigation channel which runs through the interior of the handpiece.

In certain preferred embodiments of the invention, the handpiece is configured to be of the same general size and shape as other optical surgical instruments within the same class. Thus, surgeons using the device will be generally comfortable with the device and understand its general methods of use.

Importantly, the invention includes a unique and inventive probe attached to the distal end of the handpiece. The probe is configured such that it conveniently and precisely delivers laser energy to a defined surgical site. The probe also provides precise fluid irrigation of the surgical site, as well as controlled aspiration of ablated tissue and fluid. In this manner, the surgeon is able to perform delicate and precise procedures while at the same time controlling the important functions of laser delivery, fluid delivery, and aspiration. Within the probe is a laser delivery structure. The laser delivery structure is an optical fiber or similar light conveying means. The laser delivery structure is capable of conveying a pulsed laser beam. Within the probe, the optical fiber is encapsulated to prevent the unwanted release of laser light. Generally, for surgical uses of the type discussed herein, the wavelengths of the laser will be in the range of from about 400 nm to about 3,000 nm.

In one important aspect, the probe of the present invention has a generally ski tip-shaped distal tip. The tip is formed so that it curves up to intersect the laser light emitted from the optical fiber. The tip contains an aspiration inlet in the face of the tip. The tip is also configured such that it functions as a "photon trap." That is, to the extent that laser light passes from the end of the optical fiber and through the region in which surgery is performed, the light intersects the tip and is collected. In one presently preferred embodiment, the photon trap and the aspiration inlet are formed by a single hole in the tip which is directly in the path of the pulsed laser bean The photon trap is configured so that any percentage, including all, of the laser light passing beyond the surgical site is collected. While the percentage of light collected may be varied depending on the size and placement of the photon trap, it is preferred that the photon trap be configured for the present application such that at least about 40% of the light is collected. More preferable, the tip is configured such that at least about 75% of the laser light is absorbed and collected without being reflected. As a result of the efficient collection of the laser light, any excess heat produced by the laser light is largely absorbed by the photon trap and aspirated out of the surgical site with the irrigation fluid. The photon trap redirects the collected laser light to further emulsify the ablated tissue particles once they enter the aspiration channel.

Also within the probe is an irrigation channel which in one preferred embodiment is formed from a sleeve formed by the exterior walls of the probe. The irrigation channel has one or more openings near the distal end of the probe creating a fluid outlet that allows irrigation fluid to flow into the surgical site. The distal end of the probe is tapered and mates with the irrigation sleeve to prevent unwanted leakage of irrigation fluid. Thus, irrigation fluid is conveniently provided to a point near the surgical site. Because of the operation of the aspiration channel, the fluid flows out of the irrigation openings and into the surgical site.

As mentioned above, the probe also has an aspiration channel This channel is disposed within the body of the probe and continues onto the tip. At the tip there is an aspiration inlet which may correspond to the photon trap. A vacuum is applied to the aspiration channel in the manner conventional in that art. Thus, the tip allows the irrigation fluid and ablated tissue to be removed from the surgical site.

The irrigation channel and the aspiration channel are positioned so that they create a "closed loop" irrigation system. This system draws target tissue near the tip and directly in line with the path of the pulsing laser. Placing these structures in line with each other produces a synergistic effect where the action of the laser pulses and the suction and irrigation complement each other. In this manner, the target tissue is ablated and drawn out of the surgical site. Furthermore, the configuration of the system allows heat associated with the laser surgery to be conducted away from the surgical site by the aspirated fluid flow.

In certain preferred embodiments of the device, the laser delivery structure, the fluid delivery channel, and the aspiration channel are disposed of coaxially in the body of the device. This allows each of these functions to be made available in a controlled and efficient manner.

It will be appreciated that the probe is attached to a handle for manipulation of the probe by a surgeon. As mentioned above, the handpiece as a whole is configured and designed such that it is similar in size and shape to other similar types of surgical devices. The optical fiber running through the handpiece to the probe is attached to an external laser system This attachment is made by a conventional fiber optic attachment. The aspiration and irrigation systems of the device are also attached to an external fluid source and an external vacuum source. These attachments are made by means of conventional Luer connections. Generally, the surgeon will control the laser, aspiration, and fluid flow by means of a conventional foot pedal apparatus, such as those widely used in ocular surgical procedures. Thus, the flow of fluids and the delivery of laser light is carefully controlled by the surgeon.

Thus, it will be appreciated that the present invention provides a laser surgical handpiece which is capable of efficiently delivering laser light, irrigation, and aspiration to the surgical site. The device also inimizes dispersed laser energy and reflected light beyond the surgical site. The device provides a photon trap structure which collects a significant percentage of any stray laser light.

The above described and other features and advantages of the present invention will become more fully apparent through the following detailed description and drawings, taken together with the appended claims.

4. BRIEF DESCRIPTION OF THE DRAWINGS

In order to more filly understand the manner in which the above-recited and other advantages and objects of the invention are obtained, a more particular description of the invention briefly described above will be rendered by reference to specific embodiments thereof which are illustrated in the appended drawings. These drawings depict only typical embodiments of the invention and are not therefore to be considered limiting of its scope:

5. DETAILED DESCRIPTION OF THE INVENTION

Figure 1:
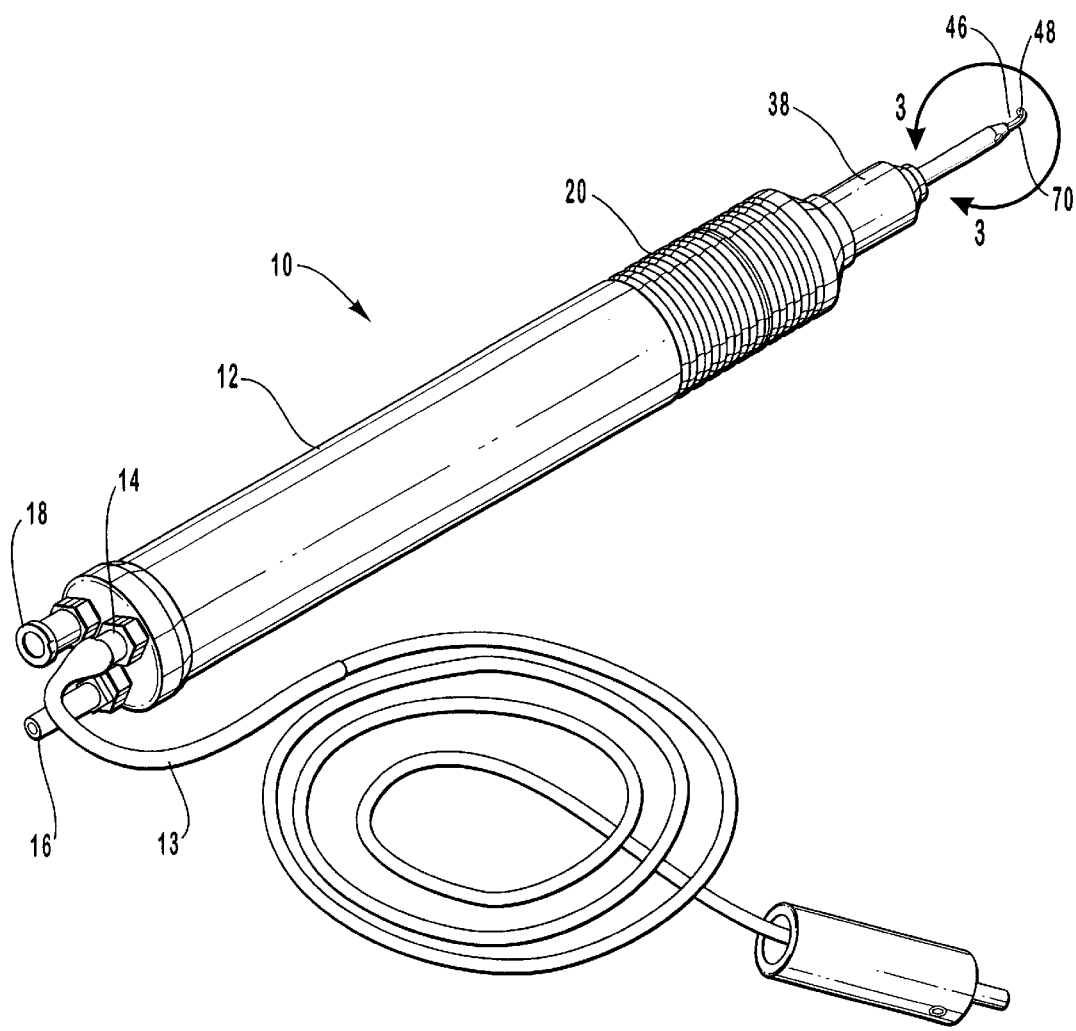
FIG. 1 is a perspective view of one embodiment of the laser surgical handpiece of the present invention illustrating standard connectors for attaching the handpiece to a source of laser light, an irrigation system, and an aspiration system.

It will be readily understood that the components of the present invention, as generally described and illustrated in the drawings herein, could be arranged and designed in a wide variety of different configurations. Thus, the following more detailed description of the embodiments of the system and method of the present invention, as represented in FIGS. 1 and 3 through 6, is not intended to limit the scope of the invention. The illustrations are merely representative of certain, presently preferred embodiments of the invention. Those presently preferred embodiments of the invention will be best understood by reference to the drawings, wherein like parts are designated by like numerals throughout.

Those of ordinary skill in the art will, of course, appreciate that various modifications to the details of the drawings may easily be made without departing from the essential characteristics of the invention. Thus, the following description of the Figures is intended only as an example, and simply illustrates one presently preferred embodiment that is consistent with the invention as claimed.

FIG. 1 illustrates one presently preferred embodiment of the laser surgical handpiece of the present invention. The laser surgical handpiece of the present invention is generally designated 10 in FIG. 1. As mentioned above, the laser surgical handpiece is specifically configured for use in cataract or other similar types of ocular surgery. However, it will be appreciated that present invention is also adaptable for use in other types of medical procedures. As illustrated in FIG. 1, the device includes a handle 12. The handle 12 is configured such that it is familiar in size and configuration to medical professionals. While the handle 12 illustrated in FIG. 1 is generally cylindrical in shape, other shapes and configurations also fall within the scope of the present invention. For example, the handle 12 could be generally square or rectangular in cross section, or could be hexagonal or octagonal in cross section. The handle 12 is also provided with a grip 20. The grip 20 as illustrated is comprised of a series of grooves cut or molded into the exterior of the handle 12. Any type of grip could be used in connection with the present invention. For example, the grip could be formed of a separate piece and then placed over the exterior of the handle 12.

At the distal terminus of the handle 12 is illustrated a cap 38. Cap 38 simply forms the distal end of the handle 12. As will be discussed in additional detail below, the cap 38 also contains and covers the proximal end of the probe 30.

At the proximal end of the handle 12 is provided the necessary connections to the laser surgical handpiece. These connections include laser connection 14. The laser connection 14 is attached to an optical fiber which runs the length of the handle 12 and probe 30 and which will be described in further detail below. The laser connection 14 is configured such that it is attachable to a standard laser attachment line 13. The laser attachment line 13 in turn conveys laser light from an external laser source (not shown). In this manner laser light is conveyed through attachment line 13, into laser attachment 14, which in turn conveys the laser light through an optical fiber disposed within the laser surgical handpiece such that laser light is delivered to the surgical site, generally designated 46 in FIG. 1. Suitable optical fibers are well known and commercially available.

Laser attachment 14, through laser attachment line 13, is connected to a high powered surgical laser (not shown). Generally, surgery of the type described herein is conducted with pulsed laser light having a wavelength between about 400 nm and about 3,000 nm. Lasers of this type general pulse at between 10–30 Hz. Various types of lasers have been used in surgery and in eye surgery, however Nd-YAG lasers have proven to be particularly useful in performing cataract surgery. Thus, in a preferred embodiment, the device is designed and configured to employ a Nd-YAG laser and to conduct the output of an Nd-YAG laser to the surgical site 46.

Also illustrated in FIG. 1 is an irrigation attachment 16. Irrigation attachment 16 is preferably a standard male Luer connection. This attachment 16 is configured and designed to be attached to an external source of irrigation fluid, such as saline solution. As will be more fully described below, the irrigation attachment 16 is in fluid communication with an irrigation channel 50 (FIGS. 4, 5, 6) which conducts irrigation fluid through the handle 12 and probe 30 to the surgical site 46.

Similarly, FIG. 1 illustrates an aspiration attachment 18. Aspiration attachment 18 is designed and configured to be attached to an external source of vacuum As illustrated, aspiration attachment 18 is a standard female Luer connection. Once again, as with the irrigation attachment 16, aspiration attachment 18 is in fluid communication with an aspiration channel 60 (FIGS. 4, 6) which travels through the interior of the handle 12 and the probe 30 in order to provide suction at the surgical site 46.

In the illustrated embodiment, handle 12 is made from a solid piece of plastic with pathways drilled for laser, irrigation, and aspiration. As mentioned above, these pathways run from the attachments 14, 16, & 18 to the probe 30. The pathways may be drilled using standard precision drilling methods. Alternatively, the handle 12 may be formed from a molded piece of plastic with the aforementioned pathways molded into to the handle by standard molding techniques.

While molded or drilled plastic handles 12 are presently preferred, it would also be possible to form the handle 12 from any other material which is suitable for use in a surgical environment. For example, handle 12 may be made from stainless steel or another solid material commonly used to manufacture surgical devices with drilled or molded pathways.

The handle 12 may also be provided with a stainless steel cap 38. The cap 38 and the handle 12 may be joined by an adhesive or by threaded attachment. The cap 38 is provided in order to securely hold the various functional elements of the device securely in place. The cap 38 also provides a smooth surface near the interface between the handle and the surgical site.

Laser surgical handpiece 10 may be disposable or reusable depending on the type of material and expense and method of manufacture of the handpiece 10. A disposable embodiment would be nearly entirely constructed of mass produced molded plastic components while a reusable embodiment would have drilled pathways and be made from expensive materials such as stainless steel.

Attached to the distal end of the handle 10 is the probe 30. The probe 30 contains key elements of the present invention and will be the focus of the discussion which follows. In the embodiment illustrated in FIG. 1, the probe 30 has a generally cylindrical body 32. Extending distally beyond the body 32 is a ski-shaped tip 70. As will be described in further detail below, the probe 30 provides the distal terminus 42 for the fiber optic which carries the laser through the device, the irrigation channel, and the aspiration channel. Importantly, the probe also includes a photon trap 48.

Figure 2:
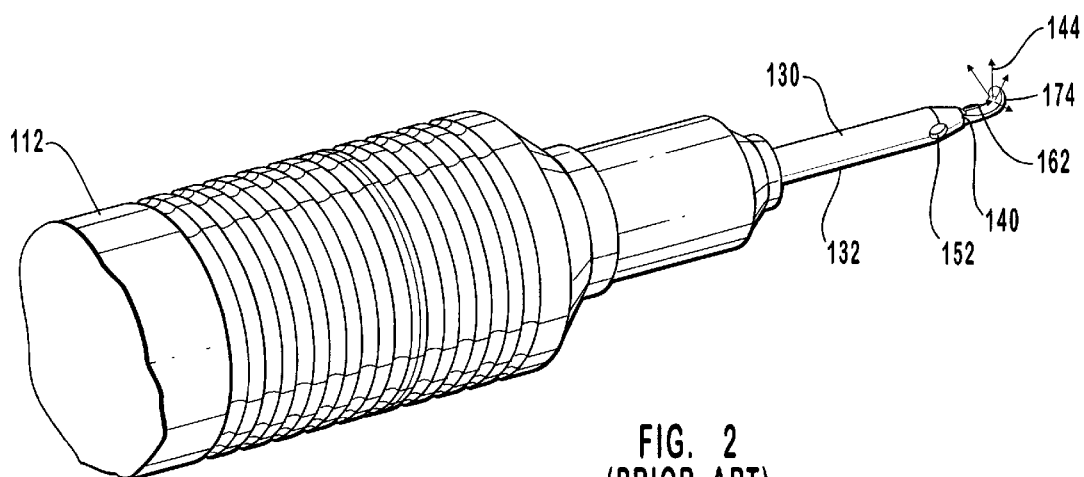
FIG. 2 is a cut-away perspective front-end view illustrating a prior art device for use in ocular laser surgery.

In order to better understand the advancements made in the current invention, it is useful to provide an illustration of a sample of the prior art in this field. Referring now to prior art FIG. 2, handle 112 is illustrated. Handle 112 is a conventional surgical handle widely used in this type of surgical procedures. As illustrated in FIG. 2, the probe 130 differs in configuration from the improved and inventive probe 30 of the present invention. The prior art probe 130 has a body 132. Body 132 contains an irrigation channel and an aspiration channel (not shown). Body 132 also contains an optical fiber (not shown). Fluid from the irrigation channel exits the body 132 through irrigation outlet 152. The irrigation fluid then flows generally distally and is aspirated through aspiration inlet 162. In this manner the surgical site receives a constant fluid flow.

Laser light also exits the body 132. As illustrated in FIG. 2, the prior art tip 134 is configured as shown with the tip curving upward or with the tip ending bluntly. Optic fiber 140 delivers laser light to a surgical site in a manner similar to that of the current invention. However, prior art device 110 has no photon trap, but relies solely on reflection to control stray laser light 144. Thus, laser light 144 may reflect into undesired tissues and cause significant damage. Furthermore, because a significant percentage of laser light 144 is not being used to ablate tissue, a higher powered laser is needed to compensate for the wasted laser light.

As further illustrated in FIG. 2, irrigation outlet 152 and aspiration inlet 162 are configured so that tissue is drawn to the path of the pulsing laser. However the pulsing action of the laser pushes the ablated tissue toward the distal end of the tip 174 while the irrigation flow pulls the tissue toward the proximal end of the tip 162. Thus, in prior art device FIG. 2, the irrigation flow and the pulses of the laser work against each other requiring increased energy for ablation and removal of the target tissue. These opposing forces also reduce the control of the surgeon and the predictability of the surgical procedure.

Figure 3:
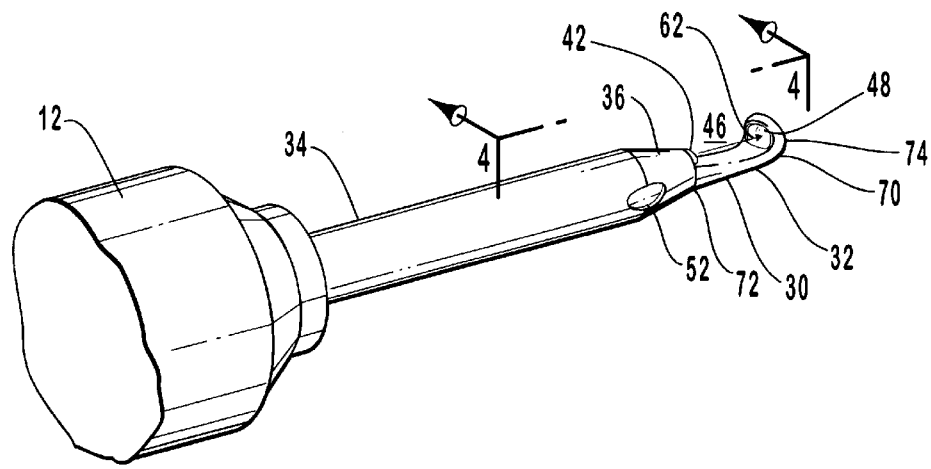
FIG. 3 is perspective view of a portion of the laser surgical handpiece illustrating one embodiment of the probe of the device and including the portion of the device designated 3—3 in FIG. 1.

The improvement provided by the present invention can be better understood with reference to FIGS. 3 through 6. Referring specifically to FIG. 3, probe 30 is illustrated. In the illustrated embodiment, the probe 30 has an elongated, generally cylindrical body 32. Body 32 has a proximal end 34 and a distal end 36. Extending distally from the body 32 is tip 70. Tip 70 has a proximal end 72, a distal end 74. In the illustrated embodiment, body 32 and tip 70 are made from a single piece of stainless steel formed as shown. In other embodiments, body 32 and tip 70 may be made from other materials commonly used in surgical instruments. Body 32 and tip 70 may also be constructed from two or more pieces.

As illustrated in FIG. 3, an irrigation outlet 52 is formed in the housing of body 32 of the tip 70. The irrigation outlet 52 is in fluid communication with an irrigation channel 50 illustrated in FIGS. 4–6. Thus, during operation of the device, irrigation fluid will exit irrigation outlet 52 and flow through the vicinity of the surgical site 46, providing a critical constant source of irrigation during surgery.

FIG. 3 also illustrates the terminus or outlet 42 of the optical fiber 40. As mentioned above, and as illustrated in additional detail in FIGS. 4–6, an optical fiber 40 is disposed within the handpiece 10 and carries laser light to the terminus 42. At this point the laser light exits the device and provides a cutting force in the surgical site 46.

Also illustrated in FIG. 3 is the aspiration inlet 62. Aspiration inlet 62 is in fluid communication with the aspiration attachment 18 by way of aspiration channel 60. Thus, when the device is connected to a source of vacuum, suction is provided through the aspiration inlet 62. By application of the vacuum, irrigation fluid and debris resulting from the surgical procedure are aspirated through aspiration inlet 62.

In the embodiment of the device illustrated in FIG. 3, the aspiration inlet 62 also functions as a photon trap 48. That is, the opening is configured such that a large percentage of any excess laser light is collected within photon trap 48. In this manner, deflected and stray laser light is largely controlled. It will be appreciated that this significantly increases the safety, effectiveness, and usefulness of the laser surgical handpiece of the present invention.

Figure 4:
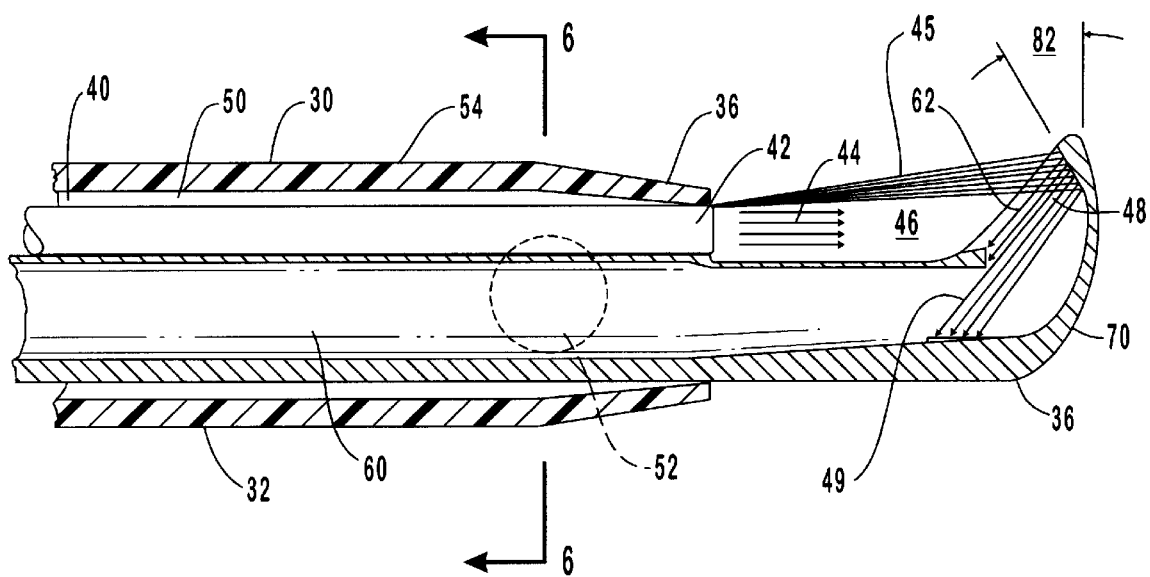
FIG. 4 is longitudinal cross-sectional view of the embodiment of FIG. 3 taken along line 4—4.

Reference is now made to FIG. 4 which is a longitudinal cross section of probe 30 taken along line 4—4 of FIG. 3. In FIG. 4, the internal structure of the probe 30 is illustrated. The laser light delivery structure of the present invention is comprised an optical fiber 40 shown in FIG. 4. FIG. 4 also illustrates irrigation channel 50 and aspiration channel 60 which are located within the body 32 of the probe 30. The optical fiber 40 runs the length of the structure 10 and, as mentioned above, is connected to an external surgical laser. The optical fiber 40 is selected such that it is capable of efficiently and effectively conveying laser wavelengths from about 400 nm to about 3,000 nm. While the laser delivery structure disclosed in the accompanying drawings is an encapsulated optical fiber, the present invention also encompasses other means of delivery of laser energy, including mirrors, prisms, or other optical structures.

In the embodiment illustrated FIG. 4, irrigation channel 50 is formed by a flexible polymeric irrigation sleeve 54 which forms the exterior of body 32. The distal end of the body 36 is tapered so that the irrigation sleeve 54 mates with the distal end of the body 36 and forms a waterproof seal. In other embodiments, irrigation channel 50 may be formed by a passageway molded or drilled within the body 32. In still other embodiments, irrigation channel 50 may formed by a tube running through the body 32.

Near the distal end of the body 36, is located an irrigation outlet 52. In the illustrated embodiment, irrigation outlet 52 is created by two holes punched into the irrigation sleeve 54 on opposite sides of the probe 30. In other embodiments the irrigation outlet 54 may be formed from one or more holes cut into irrigation sleeve 54 at positions other than those illustrated. In still other embodiments the irrigation outlet 52 may be formed from holes cut into the aforementioned tubing or passageways. As discussed previously, the irrigation outlets 52 provide a source of critical fluid flow to the surgical site 46.

In FIG. 4, tip 70 projects distally (forward) from the distal end of body 36 in a longitudinal manner. Tip 70 then projects substantially upwardly so that a structure resembling a ski tip is formed. The tip continues upward so that tip 70 intersects the pathway of laser light 44 exiting the optical fiber 40 at its distal terminus 42. In the illustrated embodiment, tip 70 and body 32 are formed from one single piece of stainless steel tubing. The tubing is tapered near the distal end of the body 32 and somewhat flattened through the tip 70 portion. The end of the tubing is curved, rounded, and sealed using standard metal working techniques. In other embodiments the body 36 and tip 70 may be formed from two or more sections of stainless steel tubing or custom molded from other suitable materials used in surgical instruments.

Aspiration channel 60 is located in the body 32 of probe 30. In the illustrated embodiment, aspiration channel 60 is formed by the same stainless steel tube that forms the body 32 and the tip 70. Aspiration channel 60 continues through the body 32 to the distal end of the tip 70. A hole or series of holes cut into the top surface of the tip 70 near the distal end of the tip 74 forms aspiration inlet 62. In the illustrated embodiment aspiration inlet 62 is formed by a single generally circular hole. But in other embodiments aspiration inlet 62 may consist of one or more holes of varying shapes. The aspiration outlet 62 is directly in the path of laser light 44 so that target tissue is drawn into the path of laser light 44.

Laser light 44 exits laser delivery structure 40 at terminus laser outlet 42. The laser light 44 is used as the cutting force during surgery. It is apparent that the laser beam must be controlled in order to avoid accidental damage to tissues not directly involved in the surgery. In addition, as previously mentioned, as light exists the terminus 42, it tends to disperse somewhat. Unless this dispersed light is collected, it will travel out of the surgical sight and may damage other tissue.

For these reasons, the present invention provides a unique structure for collecting laser light which has passed through the surgical site 46. This structure is a photon trap 48 located on the tip 70 directly in the path of laser light 44. In the illustrated embodiment, a nearly circular hole cut into top surface of the tip 76 near the distal end of tip 74 forms the photon trap 48. It will be appreciated that photon trap 48 may be configured so that any percentage, including all, of the laser light emitted by the device may be collected. In one preferred embodiment, photon trap 48 is positioned and configured such that a relatively large percentage of the laser light emitted by the device, such as at least 40%, will be collected. More preferably, the photon trap is positioned and configured such that at least 75% of laser light 44 leaving optical fiber 40 enters and is collected in photon trap 48. In the illustrated embodiment photon trap 48 uses the opening in tip 70 also used for aspiration inlet 62. In other embodiments of the device, however, the two functions may be provided by separate structures. The photon trap 48 redirects laser light 44 into the aspiration channel 60 so that any ablated tissue that is in the aspiration channel 60 is further emulsified by the recycled laser light 44 thereby recycling laser light 44 that would otherwise be wasted and making the device more efficient. Other laser light 44 is absorbed by photon trap 48 within the aspiration channel 60 and is partially converted to heat. This heat is rapidly removed from the surgical site by the flow of the irrigation fluid through the aspiration inlet 62.

Figure 5:
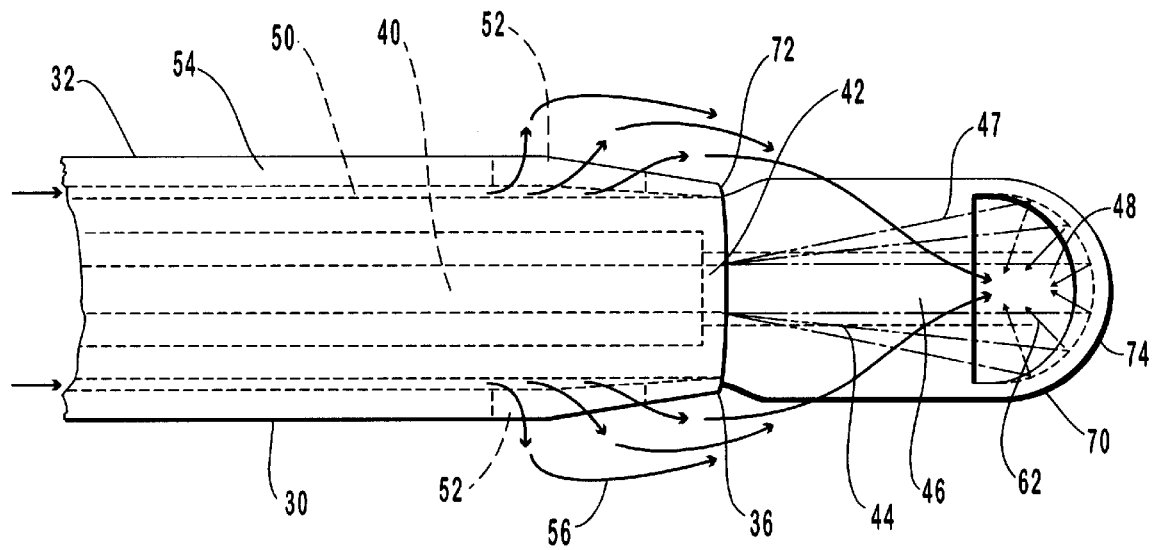
FIG. 5 is a top plan view of the embodiment of FIG. 3 illustrating the location of inner components of the device in dashed lines and also generally illustrating the flow of fluid and laser light during operation of the device.

FIGS. 4 and 5 depict laser light that is diverging (45 and 47) from the main beam (44). The entrance hole (62) is sized to capture a percentage of the laser energy (45 and 47) and also the main beam (44). In the illustrated embodiment, the tip 70 is projected in a proximal direction such that the tip forms an angle designated 82 in FIG. 4. In a presently preferred embodiment, angle 82 is approximately 30°. At this angle laser light striking the tip 70 is deflected to follow substantially the path 49 and is thereby largely contained within the photon trap 48. In other embodiments this angle will be varied depending on the size, shape, and location of photon trap 48.

Figure 6:
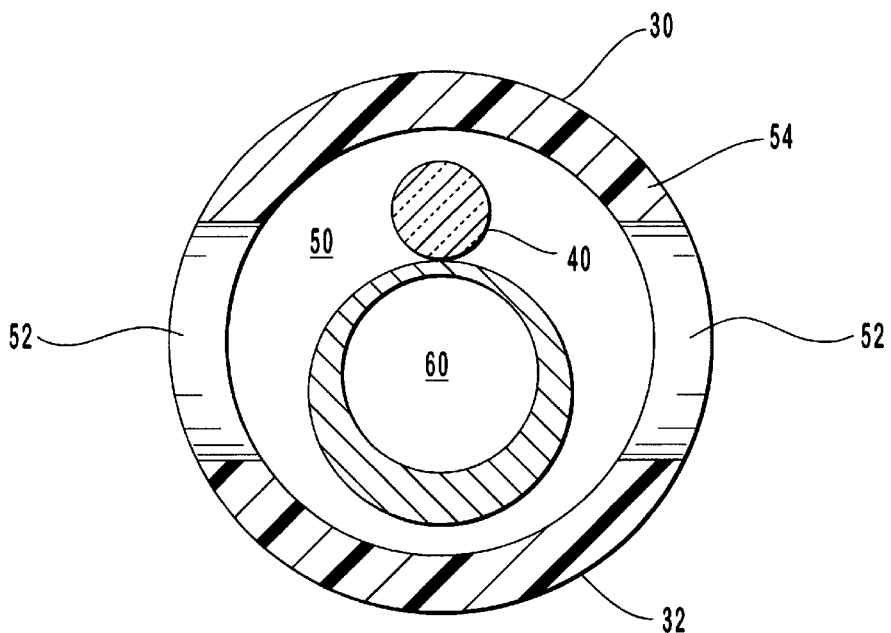
FIG. 6 is a latitudinal cross-sectional view of the embodiment of FIG. 4 taken along line 6—6.

FIG. 6 is a cross section of probe 30 taken along line 6—6 of FIG. 4. FIG. 6 is provided to better illustrate how probe 30 is constructed. In the illustrated embodiment, aspiration channel 60 is disposed within the interior of the probe 30. Aspiration channel 60 carries fluid and debris away from the surgical site 46 and ultimately out of the device through aspiration attachment 18. Disposed directly above the aspiration channel 60 is optical fiber 40. As mentioned above, the optical fiber 40 is of conventional construction and configuration. An irrigation sleeve 54 is placed over the aspiration channel 60 and laser delivery structure 40. Irrigation fluid flows within the irrigation channel 50 formed by the space between the irrigation sleeve 54 and the other structures. Irrigation outlets 52 allow irrigation fluid to flow out of the channel into the surgical site 46. The laser delivery structure 40, irrigation channel 50, and aspiration channel 60 are all contained within the body 32 and run generally coaxially.

The operation of the present invention can be fully appreciated with reference to FIG. 5. FIG. 5 is a plan view of probe 30 illustrating the inner location of the optical fiber 40, the irrigation channel 50, the aspiration channel 60, and the irrigation outlets 52.

During operation of the device, laser light 44 is directed along the optical fiber 40. The laser light 44 exits the optical fiber 40 at the terminus 42 of the fiber. The laser light 44 is directed through the surgical site 46 and is used to conduct the surgical procedure. In the context discussed above, the laser light 44 is used to remove cataracts from the lens of an eye. However, it will be appreciated that the present invention may also be adapted for use in other types of surgery.

At the same time that the laser light 44 is provided, irrigation fluid 56 flows out of the device by way of the irrigation channel 50 and the irrigation outlets 52. The fluid is directed through the surgical site 46 by the suction provided by at the aspiration inlet 62. This provides a closed loop system where ablated tissue and any heat generated during the surgery is immediately aspirated from the surgical site 46. Aspiration at this location also brings target tissue in line with the pulsing laser light 44. The laser pulses are complimented by the action of the closed loop irrigation system as the pulses from the laser and the flow of the irrigation fluid push the ablated tissue toward the aspiration inlet 62. This arrangement causes a synergistic effect where substantially less energy is required to ablate target tissue when compared to conventional devices.

Finally, as illustrated in FIG. 5, excess or deflected laser light 44 is collected within the photon trap 48 located at the tip 70 of the device. The laser light 44 thus collected is prevented from causing damage to surrounding tissues, or being deflected such that it impacts medical personnel performing the surgical procedure. Furthermore, the collected laser light 44 is redirected toward aspirated tissue in the aspiration channel 60 thereby increasing the efficiency of the device.

In summary, it will be appreciated that the present invention provides a laser surgical handpiece which overcomes some of the problems with the exiting art. In particular, the present invention provides a laser surgical handpiece which is capable of efficiently delivering laser light, irrigation, and aspiration to a surgical site. The present invention also provides a handpiece which includes a structure capable of minimizing dispersed laser energy and reflected light beyond the surgical site. The present invention collects stray laser light and removes the energy from the eye. This is accomplished by the use of irrigation and suction to complement the action of the laser. It will be appreciated that the present invention can also be easily manipulated by a surgeon.

What is claimed and desired to be secured by United States Letters Patent is:

1. A method for performing a surgical procedure comprising:
    a) positioning a target tissue inside a probe wherein the probe comprises a body with a proximal end and a distal end, a laser delivery structure disposed within the body and having a laser outlet at or near said distal end, an irrigation fluid delivery channel disposed in the body having a fluid outlet at or near said distal end, an aspiration channel disposed in the body having an aspiration inlet and an aspiration outlet, wherein said aspiration inlet and said irrigation delivery channel combine to form a closed loop irrigation system when the probe is in use, and a tip extending distally beyond said distal end of the body, the tip including a photon trap configured such that laser light emitted from the laser delivery structure is collected within the photon trap wherein the laser light collected within the photon trap is directed to further emulsify tissue that has been drawn into the aspiration channel;
    b) energizing the laser delivery structure with short pulses of laser light sufficient to ablate a target tissue into particles; and
    c) applying aspiration to the aspiration channel and irrigation fluid to the irrigation channel such that the target tissue is drawn into the path of the pulsing laser and into the aspiration channel.

2. The method of claim 1 wherein the photon trap is configured to collect any selected percentage of the laser light emitted from the laser delivery structure.

3. The method of claim 1 wherein the laser delivery structure, the aspiration inlet, and the irrigation outlet are positioned such that tissue on which surgery is performed is drawn away from the laser delivery structure while being positioned into the path of the laser.

4. A probe for use in laser surgery comprising:
    a body with a proximal end and a distal end;
    a laser delivery structure disposed within the body and having a laser outlet at or near said distal end;
    an irrigation fluid delivery channel disposed in the body having a fluid outlet at or near said distal end;
    an aspiration channel disposed in the body having an aspiration inlet and an aspiration outlet; and
    a tip extending distally beyond said distal end of the body, the tip including a photon trap configured such that laser light emitted from the laser delivery structure is collected within the photon trap and wherein the photon trap and the aspiration inlet utilize a single opening in said tip;
    wherein said photon trap is configured such that the laser light collected within said photon trap is redirected to further emulsify tissue that has been drawn into said aspiration channel.

5. A probe as in claim 4 wherein said photon trap is configured such that it collects not less than approximately 40% of the laser light emitted from said laser delivery structure.

6. A probe as in claim 4 wherein said photon trap is configured such that it collects not less than 75% of the laser light emitted from the laser delivery structure.

7. A probe as in claim 4 wherein said housing has a longitudinal axis, the tip extending outwardly from said housing in a direction of the longitudinal axis then curving upwardly so that said tip intersects the laser light beam.

8. A probe as in claim 4 wherein said laser delivery structure comprises an optical fiber.

9. A probe as in claim 8 wherein said optical fiber is encapsulated.

10. A probe as in claim 4 wherein said irrigation fluid delivery channel is formed by an irrigation sleeve surrounding the housing, the irrigation sleeve and distal end of said housing configured such that the irrigation sleeve mates to said distal end.

11. A probe as in claim 4 wherein said laser delivery structure, said fluid delivery channel, and said aspiration channel are all disposed coaxially within said housing.

12. A probe as in claim 4 wherein said laser delivery structure is capable of conveying laser wavelengths from about 400 nm to about 3,000 nm.

13. A probe as in claim 4 wherein said probe is configured to be attached to a handle to for a laser surgical handpiece, said handle being configured and dimensioned to be coupled to surgical equipment providing an irrigation system, an aspiration system, a laser system, and a foot pedal apparatus capable of controlling each of Saadi systems independently or in combination.

* * * * *